US000001043H

United States Statutory Invention Registration [19]

[11] Reg. Number: H1043

[43] Published: Apr. 7, 1992

Speranza et al.

[54] BIS-HYDROXY DIAMIDES AND METHODS THEREFOR

[75] Inventors: George P. Speranza, Austin; Jiang-Jen Lin, Houston, both of Tex.

[73] Assignee: Texaco Chemical Company, White Plains, N.Y.

[21] Appl. No.: 465,666

[22] Filed: Jan. 16, 1990

[51] Int. Cl.[5] ..... C07C 235/08

[52] U.S. Cl. ..... 564/156; 564/160

[58] Field of Search ..... 564/156, 158, 160

[56] References Cited

U.S. PATENT DOCUMENTS

| | | | |
|---|---|---|---|
| 4,123,422 | 10/1978 | Erikson et al. | 528/273 |
| 4,373,085 | 2/1983 | Bolze et al. | 528/291 |
| 4,397,991 | 8/1983 | Drawert et al. | 525/167 |
| 4,611,051 | 9/1986 | Hayes et al. | 528/295.3 |
| 4,617,342 | 10/1986 | Poppe et al. | 524/606 |
| 4,656,242 | 4/1987 | Swan et al. | 528/295.3 |

OTHER PUBLICATIONS

Aoso et al., *Chemical Abstracts* 110:222613f (1989).

Fuji Photo Film Co., *Chemical Abstracts* 99:124243v (1983).

Habermeier et al., *Chemical Abstracts* 92:59762c (1980).

Osdena et al., *Chemical Abstracts* 65:12204g (1966).

Yangol et al., *Chemical Abstracts* 75:49618v (1971).

H. Wenker, "The Synthesis of $\Delta^2$-Oxazolines and $\Delta^2$-Thiazolines from N-Acyl-2-Aminoethands," *J.A.C.S.*, vol. 57, Jun. 1935, pp. 1079-1080.

Texaco Chemical Company Data Sheet, "Amides from Diglycolamine® Agent," 1981.

J. R. Flesher, Jr., "Polyether Block Amide: High-Performance TPE," *Modern Plastics*, Sep. 1987, pp. 100-110.

*Primary Examiner*—Richard D. Lovering
*Assistant Examiner*—Joseph D. Anthony
*Attorney, Agent, or Firm*—Jack H. Park; Kenneth R. Priem; David L. Mossman

[57] ABSTRACT

Novel bis-hydroxy diamides having the formula:

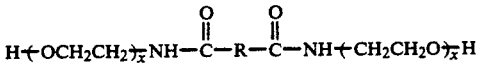

where R is an alkyl or aryl moiety having from 3 to 10 carbon atoms and where x ranges from 1 to 6 may be produced by reacting dicarboxylic acids with polyethylene glycol monoamines. Suitable dicarboxylic acids include adipic acid, terephthalic acid, isophthalic acid, t-butyl isophthalic acid, 1,1,3-trimethyl-5-carboxy-3-(p-carboxyphenyl)indane, and mixtures thereof. Suitable monoamines include diethylene glycol monoamine, also known as Diglycolamine® amine (DGA); triethylene glycol monoamine (TEGMA) and tetraethylene glycol monoamine ($T_4$EGMA), among others. The resulting bis-hydroxy diamides are useful to make hydroxy-terminated polyamides and as fuel additive corrosion inhibitors. The diamides have unusual solubility properties.

3 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

BIS-HYDROXY DIAMIDES AND METHODS THEREFOR

CROSS-REFERENCES TO RELATED APPLICATIONS

This application is related to U.S. patent application Ser. No. 07/465,290, filed of even date, now U.S. patent No. 5,082,924 relating to mixed polyamide-esters made from the novel bis-hydroxy diamides of the subject application; and U.S. Pat. application Ser. No. 07/465,682, filed of even date, now U.S. Pat. No. 4,996,315 relating to the synthesis of cyclic compounds from polyethylene glycol monoamines and dibasic acids.

FIELD OF THE INVENTION

The invention relates to by-products from the manufacture of polyoxyalkyleneamines, and, in one aspect, more particularly relates to bis-hydroxy amides prepared by the reaction of such by-products with carboxylic acids.

BACKGROUND OF THE INVENTION

Triethylene and tetraethylene glycol diamines may be continuously produced from glycols catalytically. The triethylene glycol diamine and tetraethylene glycol diamine products are known under the trade names JEFFAMINE® EDR-148 Amine and JEFFAMINE® EDR-192 Amine, respectively, as made by Texaco Chemical Co. These materials are useful as intermediates in the preparation of hydrophilic nylon resins, and as epoxy curing agents. However, in the production of polyethylene glycol diamines, due to moderate conversions, there are also produced significant quantities of by-products, bottoms products or residues, and it would be beneficial if uses for these materials, such as triethylene glycol monoamine and tetraethylene glycol monoamine, could be discovered.

It is, of course, known to react materials having active hydrogens with compounds having carboxylic acid groups. For example, U.S. Pat. No. 4,123,422 teach amide modified saturated polyester polyols where the polyester polyol backbone is made from a polyhydric alcohol having 2 to 15 carbon atoms and a polybasic carboxylic acid having 4 to 14 carbon atoms. After the backbone is formed, it is modified with a primary or secondary amine of the formula $N(H)(R)_a(C_yH_{2y}OH)_b$, where R is a hydrogen or an alkyl group of 1 to 4 carbon atoms, y is 2 or 3, a is 0 or 1, b is 1 or 2, and the sum of a+b is 2. These amine modified saturated polyester polyols are useful in two-package urethane coating systems. A crystalline polyamide which has improved tensile strength and which has a heat deflection temperature in excess of 240° C. when filled is formed from dicarboxylic acid compounds comprising compounds of terephthalic acid and isophthalic acid in a molar ratio of at least 80:20 to about 99:1 and diamines comprising hexamethylene diamine and trimethylhexamethylene diamine in a molar ratio of about 98:2 to about 60:40, according to U.S. Pat. No. 4,617,342.

Hot melt adhesives are also related to these kinds of materials. For example, U.S. Pat. No. 4,656,242 describes that poly(ester-amide) polymers made from an acid component and a substantially equivalent amount of an amine and a diol component are suitable as hot melt adhesives for holding plastics. The acid component has 10–80 equivalent percent of a dimer acid having about 36 carbon atoms and 40–90 equivalent percent of a linear dicarboxylic acid. The amine and diol component has from 40–90 equivalent percent of an organic diamine and 10–60 equivalent percent of a diol. Also of interest is U.S. Pat. No. 4,611,051 which teaches poly(ester-amide) hot-melt adhesives prepared from condensation of a mixture of polymeric fatty acids and 1,18-octadecanedicarboxylic acid, and a substantially equivalent proportion of a mixture of a polyamine and a polyol. Suitable polyamines include ethylenediamine, 1,3-propanediamine, 1,4-butanediamine, 1,6-hexamethylene-diamine, piperazine, and 4,4'-methylene-bis-(cyclohexylamine). Appropriate diols are ethylene glycol, 1,3-propanediol, 1,4-butanediol, 1,6-hexamethylenediol, cyclohexane-methanol, polyethylene glycol and polybutylene glycol.

In U.S. Pat. No. 4,373,085 polyesteramides are prepared by condensing (A) dimerized fatty acids having 16 to 44 carbon atoms, (B) a diamine having a formula of $NH_2—R—NH_2$ where R is an aliphatic hydrocarbyl having 3 to 36 carbon atoms and (C) aminoethoxyethanol and at least one dicarboxylic acid having the formula R"OOC—R'—COOR" where R' is a hydrocarbyl of 4 to 12 carbon atoms and R" is H or alkyl having 1 to 8 carbon atoms. U.S. Pat. No. 4,397,991 describes similar products. The polyesteramides are used as adhesives which combine good elongation, quick setting times and good low temperature flexibility.

A good, general background article about these amide materials is J. R. Flesher, Jr., "Polyether Block Amide: High-Performance TPE," *Modern Plastics*, September, 1987 pp. 100–110, where the family of engineering-grade thermoplastic elastomers based on block copolymers of polyethers and polyamides is discussed.

SUMMARY OF THE INVENTION

Accordingly, it is an object of the present invention to provide a process for the production of novel materials made from by-products of polyethylene glycol diamine production.

It is another object of the present invention to provide novel materials which will have uses in the production of mixed polyamide-esters and polyurethanes by reaction with polyisocyanates.

Another object of the invention to provide a method for making these novel materials that is very simple.

In carrying out these and other objects of the invention, there is provided, in one form, novel bis-hydroxy diamides having the formula:

$$H\left(OCH_2CH_2\right)_x NH—\overset{O}{\overset{\|}{C}}—R—\overset{O}{\overset{\|}{C}}—NH\left(CH_2CH_2O\right)_x H$$

where R is an alkylene moiety having from 3 to 34 carbon atoms or an arylene moiety having from 6 to 34 carbon atoms and where x ranges from 3 to 6.

DETAILED DESCRIPTION OF THE INVENTION

It has been discovered that the polyethylene glycol monoamines that are produced as by-products in the production of JEFFAMINE® EDR amines, by-products such as triethylene glycol monoamine and tetraethylene glycol monoamine, as well as materials such as diethylene glycol monoamine, may be advantageously reacted with dicarboxylic acids to form novel bis-hydroxy diamides. These novel bis-hydroxy diamides are useful to make mixed polyamide-esters and polyurethanes, as is seen in companion patent application Ser. No. 07/465,290, filed of even date, incorporated by reference herein.

The novel bis-hydroxy diamides of this invention may be made according to the reaction that may be schematically diagrammed as:

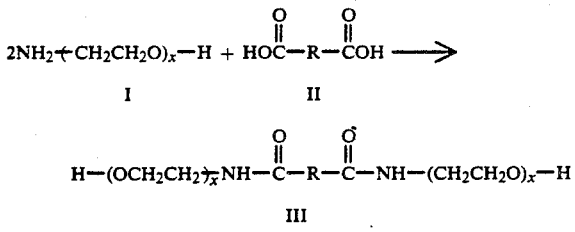

where (I) are the polyethylene glycol monoamine by-products or other materials where x ranges from 2 to 6, preferably 2 to 5 and most preferably from 3 to 4. When x is 2, the compound is diethylene glycol monoamine. When x is 3 and 4, the compounds are triethylene glycol monoamine and tetraethylene glycol monoamine, respectively.

Compound (II) is the dicarboxylic acid and R may be an alkylene moiety having from 3 to 34 carbon atoms in one embodiment, in one aspect from 4 to 20 carbon atoms, and in a further aspect from 4 to 9, or an alkylene moiety having from 6 to 34 carbon atoms. In another aspect of the invention, the dicarboxylic acid may be selected from the group consisting of adipic acid, terephthalic acid, isophthalic acid, t-butyl isophthalic acid, 1,1,3-trimethyl-5-carboxy-3-(p-carboxyphenyl) indane also known as phenylindane dicarboxylic acid or PIDA and mixtures thereof. In yet another aspect, the dicarboxylic acid may be "dimer" acid which is mainly a C-36 dicarboxylic acid. This product is prepared by dimerizing unsaturated fatty acids. The esters of these acids may also be used.

The novel bis-hydroxy diamides are represented as compound (III) where R and x have the meanings given above. The bis-hydroxy diamides may be made by contacting at least two moles of the polyethylene glycol monoamine for every mole of dicarboxylic acid in the presence of heat, from approximately 180° to about 250° C. as a narrower range, where a broad temperature range for this reaction is from about 160° to about 280° C. Preferably, the molar ratio of monoamine to dibasic acid is about 2:1. No catalyst is required for this reaction, although one may be yet discovered that might prove beneficial. The reaction may also be conducted at atmospheric pressure. The reaction is quite selective yielding the bis-hydroxy diamides in nearly quantitative yield. The products are light-colored solids or liquids, depending on the starting materials. The products and methods of this invention will be described in more detail with reference to the following examples.

EXAMPLE 1

Reaction of Adipic Acid with Two Moles of Triethylene Glycol Monoamine

To a 500 ml 3-necked flask equipped with a stirrer, thermometer and Dean-Stark trap was added 73 g. of adipic acid (0.5 moles) and 150 g. of triethylene glycol monoamine (1 mole). The contents were heated at 192°-195° C. for about one hour after which 14 ml of water was collected. After an additional three hours at 200° C., a total of 15.4 ml of water was collected. The product was heated an additional hour at 200° C. and 30 mm. The off-white solid weighed 203.5 g, was water soluble and melted at 34° C. The total acetylatables was 4.92 meq/g. which gives a molecular weight of 406 (actual 408). The saponification number was 15.41 mg. KOH/g. which was determined by refluxing with alcoholic sodium hydroxide. This indicates only 5.4% of the product reacted with potassium hydroxide—or from another point of view this amide is hard to hydrolyze—in fact, all of the hydrolysis took place at an ester linkage, since NMR showed an ester to hydroxyl linkage ratio of about 1.1 to 32.3. Thus, the reaction was not 100% amide, but was selective in the order of 95%. There was no unreacted amine. The weight average molecular weight was 407 and the number average molecular weight was 407 by Gel Permeation Chromatography (GPC); the theoretical molecular weight was 408. These results prove the selectivity involved.

EXAMPLE 2

Reaction of Adipic Acid with Two Moles of Tetraethylene Glycol Monoamine

To a 500 ml, 3-necked flask equipped with a stirrer, thermometer and Dean-Stark trap was added 73 g. of adipic acid and 193 g. of $T_4EGMA$. The contents were heated for three hours at 185°-193° C. after which 14 ml of water was collected. The product was heated at 193° C. for one hour under full aspirator vacuum. The product weighed 245.1 g. and was a water soluble wax that melted at about 30° C. The NMR spectra showed the hydroxyl to ester peak to be 23:1 and there was no amine in the product. The product appeared fairly pure, both by NMR and GPC. The weight average molecular weight by GPC was 509 and the number average was 507 (theoretical=496).

Additional examples were conducted in a similar fashion, and the reactants and product properties are summarized in Table I. Table I illustrates that the product properties depend on the starting materials.

TABLE I

| | | Diols with Amide Linkages | | | |
|---|---|---|---|---|---|
| | | | Properties | | |
| | | | Hydroxyl No. | | |
| Ex. | Carboxylic Acid | Hydroxy-amine | meq/g. | (Theory) | |
| 2 | Adipic acid | DGA | 5.9 | (6.0) | Solid, creamy, light brown, opaque |
| 3 | Terephthalic acid | DGA | 2.5 | (5.5) | Solid, brown, hard, transparent |
| 4 | Isophthalic acid t-Butyl IPA | DGA | 3.6 | (5.5) | Solid, soft, brown, transparent |
| 5 | PIDA | DGA | 3.4 | (4.0) | Solid, glass-like, transparent, brown, |

TABLE I-continued

| Ex. | Carboxylic Acid | Diols with Amide Linkages: Hydroxy-amine | Properties: Hydroxyl No. meq/g. | Hydroxyl No. (Theory) | Properties: |
|---|---|---|---|---|---|
| | | | | | brittle |
| 6 | NDC | DGA | — | — | Solid, hard, black |
| 7 | Adipic acid | TEGMA | 4.9 | (4.9) | — |
| 8 | Terephthalic acid<br>Isophthalic acid<br>t-Butyl IPA | TEGMA | 4.5 | (4.7) | Solid, creamy white |
| 9 | PIDA<br>NDC<br>Trimesic acid | TEGMA | 2.8 | (3.4) | Solid, hard, transparent, brown |
| 10 | Adipic acid | T4EGMA | — | — | Solid, creamy, white |
| 11 | Terephthalic acid | T4EGMA | 3.70 | (3.88) | Liquid, brown, transparent |
| 12 | Isophthalic acid | T4EGMA | 3.55 | (3.75) | Liquid, brown, transparent |
| 13 | t-Butyl IPA | T4EGMA | 3.30 | (3.47) | Liquid, brown, transparent |
| 14 | PIDA<br>NDC | T4EGMA | 2.84 | (2.94) | Semisolid, brown, elastomeric |

Note that the reactions of $NH_2(CH_2CH_2O)_x—H$ proceed well with aliphatic dibasic acids when x is 2, 3 or 4. When x is 2, the reaction with aromatic dicarboxylic acids is not as selective as the reactions of those compounds where x is 3 or 4. These results relate to reactions where two moles of polyethylene glycol monoamine were allowed to react with one mole of the dibasic acid. Some polymeric material is obtained, especially in the case of aromatic dicarboxylic acids, when higher reaction temperatures are required. To prepare the products of this invention more selectively, a higher ratio of polyethylene glycol monoamine to dibasic acid is suggested. Dialkyl and diaryl esters may be used instead of the corresponding dibasic acids. This fact may be noteworthy in the case of 2,6-naphthalene dicarboxylic acid where the commercial grade of the dimethyl ester is much better than the dicarboxylic acid.

The reaction of carboxylic acid with monoethanolamine is beset with ester and oxazoline formation when the reaction is heated to excess:

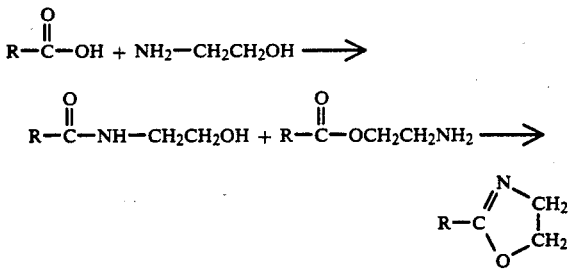

See *J. American Chemical Soc.*, Vol. 57, p. 1079 (1935). The reaction of diethylene glycol monoamine with fatty acids is a promising commercial application (see Texaco Chemical Company data sheet "Amides From Diglycolamine® Agent", 1981). The reaction of triethylene glycol monoamine with tall fatty acids involves less by-products than the corresponding reaction with monoethanolamine. The reaction of adipic acid with monoethanolamine in an attempt to prepare polyesters yielded a brittle, brown unattractive solid. Of interest in the present investigation is the preparation of bis-dihydroxydiamides which can be used to make attractive polyesters from DGA, TEGMA, $T_4$EGMA, $T_5$EGMA, etc. These products have attractive uses as adhesives, as fuel additives and as corrosion inhibitors. The bis-hydroxy amides of the present invention are also useful as chain extenders in polyurethanes, especially in water absorbing polyurethanes.

Another advantage of these products in which at least two moles of glycol amine are allowed to react with a dibasic acid is that little, if any, cyclic products are obtained. For example, if glutaric, adipic or pimelic acid is allowed to react with triethylene glycol monoamine, some "crown" like products are obtained. The reaction using adipic acid and triethylene glycol monoamine proceeds to a certain extent as shown below:

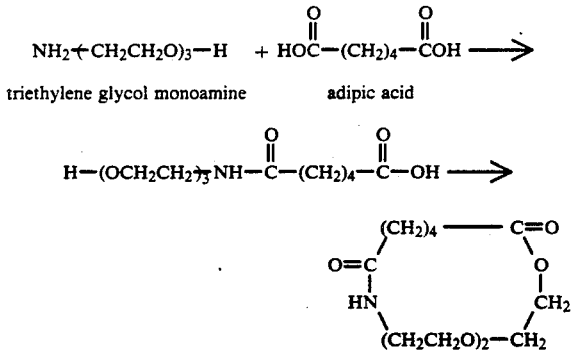

Many modifications may be made in the process of this invention without departing from the spirit and scope thereof which are defined only in the appended claims. For example, one skilled in the art may discover that particular reaction conditions or acids, which may not be explicitly recited therein, but which are nevertheless anticipated, would give desirable results.

GLOSSARY

| | |
|---|---|
| DGA | Diethylene glycol monoamine (DEGMA) or Diglycolamine® Agent made by Texaco Chemical Company. |
| IPA | Isophthalic acid. |
| NDC | Naphthalene dicarboxylic acid - esters of this acid are preferred because of their relatively higher purity. |
| TEGMA | Triethylene glycol monoamine. |
| $T_4$EGMA | Tetraethylene glycol monoamine. |

-continued

GLOSSARY

| | |
|---|---|
| $T_5EGMA$ | Pentaethylene glycol monoamine. |

We claim:

1. Novel bis-hydroxy diamides having the formula:

$$H\left(OCH_2CH_2\right)_x NH-\overset{O}{\overset{\|}{C}}-R-\overset{O}{\overset{\|}{C}}-NH\left(CH_2CH_2O\right)_x H$$

where R is an alkylene moiety having from 3 to 34 carbon atoms or an arylene moiety having from 6 to 34 carbon atoms, and where x ranges from 3 to 6.

2. The novel bis-hydroxy diamines of claim 1 where R is an alkyl or aryl moiety having from 4 to 20 carbon atoms and where x ranges from 3 to 5.

3. The novel bis-hydroxy diamines of claim 1 where R is an alkyl or aryl moiety having from 4 to 9 carbon atoms and where x ranges from 3 to 4.

* * * * *